United States Patent [19]

Schaffner

[11] Patent Number: 5,149,841
[45] Date of Patent: Sep. 22, 1992

[54] N,N,N',N'-TETRAGLYCIDYL-4,4'-DIAMINODIPHENYLMETHANES

[75] Inventor: Werner Schaffner, Riehen, Switzerland

[73] Assignee: Ciba-Geigy Corporation, Ardsley, N.Y.

[21] Appl. No.: 694,525

[22] Filed: May 1, 1991

[30] Foreign Application Priority Data

May 7, 1990 [CH] Switzerland .......... 1537/90

[51] Int. Cl.$^5$ .......... C07D 301/27; C07D 301/26; C07D 303/36
[52] U.S. Cl. .......... 549/520; 549/514
[58] Field of Search .......... 549/514, 520

[56] References Cited

U.S. PATENT DOCUMENTS

| | | | |
|---|---|---|---|
| 1,790,042 | 1/1931 | Eisleb | 549/514 |
| 3,278,561 | 10/1966 | Gaertner | 549/514 |
| 3,595,882 | 7/1971 | Bremmer | 549/514 |
| 4,373,073 | 2/1983 | Wojteck et al. | 525/507 |
| 4,540,769 | 9/1985 | Daleinsan et al. | 528/90 |
| 4,778,863 | 10/1988 | Wang et al. | 549/514 |
| 4,871,867 | 10/1989 | Hidaka et al. | 549/514 |

FOREIGN PATENT DOCUMENTS

| | | | |
|---|---|---|---|
| 143075 | 5/1985 | European Pat. Off. | 549/514 |
| 2815182 | 10/1978 | Fed. Rep. of Germany | 549/514 |
| 70881 | 5/1982 | Japan | 549/520 |
| 175481 | 10/1984 | Japan | 549/514 |
| 2077376 | 4/1987 | Japan | 549/514 |
| 2111977 | 7/1983 | United Kingdom | |

OTHER PUBLICATIONS

Patent Abstracts of Japan vol. 8, No. 178 (C-238) (1615) Aug. 16, 1984.
Patent Abstracts of Japan vol. 8, No. 34 (C-210) (1471) Feb. 15, 1984.
Patent Abstracts of Japan vol. 7 No. 285 (C-201) (1430) Dec. 20, 1983.

Kirk-Othmer vol. 9, 3rd Edition p. 277.

Primary Examiner—Joseph E. Evans
Attorney, Agent, or Firm—JoAnn Villamizar

[57] ABSTRACT

A process for the preparation of compounds of the formula I

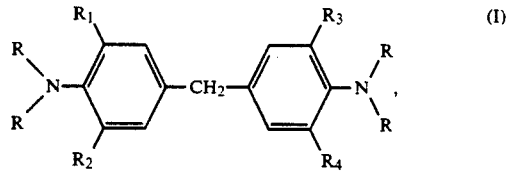

in which R is glycidyl, $R_1$ and $R_3$ independently of one another are $C_1$-$C_6$ alkyl and $R_2$ and $R_4$ independently of one another are hydrogen or methyl, wherein
(i) a diamine of the formula II

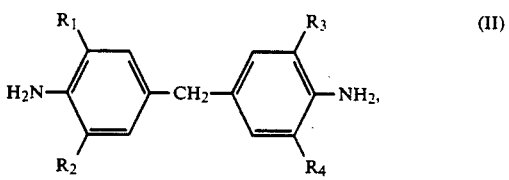

in which $R_1, R_2, R_3$ and $R_4$ are as defined above, is reacted with epichlorohydrin in a molar ratio of 1:12 to 1:40 at a temperature of 80° to 115° C. and
(ii) a phase transfer catalyst is mixed with the reaction mixture, the epichlorohydrin is subjected to distillation while being circulated and at the same time the dehydrochlorination is carried out with the addition of a concentrated, aqueous alkali metal of alkaline earth metal hydroxide solution and simultaneous removal of the water distilled off azeotropically.

12 Claims, No Drawings

N,N,N',N'-TETRACLYCIDYL-4,4'-DIAMINODIPHENYLMETHANES

The present invention relates to a process for the preparation of N,N,N',N'-tetraglycidyl-3,3'-dialkyl-4,4'-diaminodiphenylmethanes and the use of the compounds thus obtained for the preparation of cured products.

Various processes for the preparation of N-glycidylamines are known.

Thus, for example, GB-A-2 111 977 describes a process which, using trifluoromethanesulfonic acid as a catalyst, gives N-glycidylamines in relatively poor yield and with a low epoxy content and a high viscosity.

Experiments show that the reaction of aromatic amines with epichlorohydrin is in principle also possible without catalysts. However, the N-glycidylamines thus prepared have disadvantages which restrict and frequently prevent their use. First, the epoxy content of the products thus obtained is seldom close to the theoretical values for complete glycidylation, i.e. the values determined if every amine hydrogen atom were to be replaced by a glycidyl group. The actual epoxy content varies depending on the type of amine and is dependent in particular on whether other substituents are present in the molecule. Thus, for example, the epoxy content of the commercial bis(aminophenyl)methane into which glycidyl groups have been introduced is stated as 117-133 in Kirk-Othmer "Encyclopedia of Chemical Technology", 3rd Edition, Volume 9, page 277. This corresponds to an epoxy content of 79-90% of the theoretically possible value. It is known that the properties of the cured resin are dependent on the epoxy content of the uncrosslinked resin: the higher the epoxy content, the greater the crosslinking density and hence the stronger the crosslinked resin. It is clear that a higher epoxy content of the resin would be advantageous.

The second disadvantage of conventionally prepared N-glycidylamines is that they are often very viscous, probably as a result of a secondary reaction during the preparation, in which a coupling reaction takes place instead of the desired glycidylation. Such coupling reactions also give rise to the stated lower epoxy contents. The use of more highly viscous resins gives rise to difficulties, in particular in the production of fibre-reinforced composites or mouldings, frequently necessitating the use of inert diluents which reduce the viscosity.

Use of diluents is generally regarded as undesirable. Reactive diluents are those which react with the curing agent and remain in the crosslinked resin. They can have an adverse effect on the properties of the cured resin. Inert diluents are removed by evaporation prior to curing and often constitute a danger owing to their flammability or toxicity. Moreover, they can have an adverse effect on the properties of the cured resin if they are not completely removed from the resin.

An attempt was therefore made to find processes which give N-glycidylamines which have the stated disadvantages to a much smaller extent, if at all. EP-B 0 143 075 describes a process which gives products having a higher epoxy content and a lower viscosity. The catalysts used are divalent or polyvalent metal salts of nitric acid or perchloric acid, or divalent or polyvalent metal salts of a halogen-containing carboxylic acid or sulfonic acid.

It is desirable to provide a process in which the use of catalysts can be avoided, on the one hand for ecological and economical reasons and on the other hand undesirable sludge formation occurs in the stated process during working up. The low selectivity of the catalyst-free processes described above is unsuitable as a basis for a satisfactory solution to the problem.

According to the invention, it has been found that it is possible to dispense with the presence of a catalyst if the process is carried out in a suitable manner.

The present invention relates to a process for the preparation of compounds of the formula I

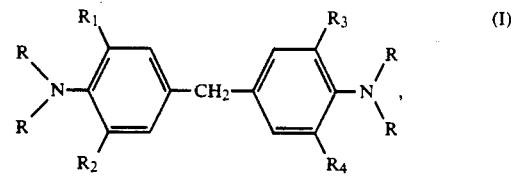

in which R is glycidyl, $R_1$ and $R_3$ independently of one another are $C_1$–$C_6$alkyl and $R_2$ and $R_4$ independently of one another are hydrogen or methyl, wherein
(i) a diamine of the formula II

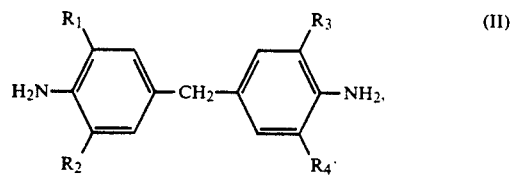

in which $R_1$, $R_2$, $R_3$ and $R_4$ are as defined above, is reacted with epichlorohydrin in a molar ratio of 1:12 to 1:40 at a temperature of 80° to 115° C. and
(ii) a phase transfer catalyst is mixed with the reaction mixture, the epichlorohydrin is subjected to distillation while being circulated and at the same time the dehydrochlorination is carried out with the addition of a concentrated, aqueous alkali metal or alkaline earth metal hydroxide solution and simultaneous removal of the water distilled off azeotropically.

The diamines of the formula II are known compounds and are described, for example, in U.S. Pat. Nos. 3,427,282 or 3,560,443.

In preferred compounds of the formula I, the substituents $R_1$ and $R_3$ or $R_2$ and $R_4$ have the same meaning. Compounds of the formula I in which $R_2$ and $R_4$ are hydrogen and those in which $R_1$ and $R_3$ are ethyl are particularly preferred.

The addition reaction of stage (i) takes place in an optimum manner, i.e. there are scarcely any detectable secondary reactions. The excess of epichlorohydrin is not critical but for economic reasons it is set at 1:40, preferably 1:20. For the reaction procedure, this means that epichlorohydrin is used as a solvent. This has the advantage that it is possible to dispense with an additional solvent, which is used in the abovementioned catalytic processes.

The reaction temperature of stage (i) is limited by the boiling point of epichlorohydrin (118° C.) and is 80°–115° C., preferably 90°–105° C. In the stated ranges, selectivity is particularly advantageous. At temperatures below 80° C., moreover, unduly long reaction times have to be accepted.

The reaction times of stage (i) are in general 5 to 15 hours, depending on the reaction temperature chosen.

As a rule, strong alkalis are used for the dehydrohalogenation. Aqueous sodium hydroxide solution is preferably used, but other alkaline reagents, such as potassium hydroxide, barium hydroxide, calcium hydroxide, sodium carbonate or potassium carbonate, can also be used. 20 to 100% by weight sodium hydroxide solution is preferably used in the process according to the invention. In general, stoichiometric amounts, i.e. 4 mol, based on the diamine of the formula II, of alkali metal or alkaline earth metal hydroxide are employed in the dehydrohalogenation, but it is advantageous to carry out elimination of hydrogen halide using up to a 25% excess (5 mol) over and above the stoichiometric amount of alkali.

In stage (ii), a phase transfer catalyst is used for the dehydrochlorination. Phase transfer catalysts, such as quaternary ammonium salts, for example tetramethylammonium chloride, tetraethylammonium chloride, benzyltrimethylammonium chloride, benzyltrimethylammonium acetate, methyltriethylammonium chloride, tetrabutylammonium chloride or tetrabutylammonium sulfate, or the corresponding phosphonium salts, quaternary ammonium bases, for example benzyltrimethylammonium hydroxide, and crown ethers, for example 12-crown-4ether (1,4,7,10-tetraoxacyclodecane), 15-crown-5ether (1,4,7,10,13-pentaoxacyclopentadecane), 18-crown-6ether or dibenzo-18-crown-6ether, are suitable. Other suitable catalysts are tertiary amines, for example 2,4,6-tris(dimethylaminomethyl)phenol, benzyldimethylamine, 1-methylimidazole, 2-ethyl-4-methylimidazole or aminopyridine.

Tertiary ammonium or phosphonium salts are preferred. These are used in the conventional amounts, for example 0.5-10, preferably 1.5 mol %, based on the diamine of the formula II.

It has now been found that, in a preferred embodiment of the process according to the invention, a weak inorganic base is concomitantly used in stage (ii). This is, for example, the bicarbonate of sodium or of potassium. An alkali metal bicarbonate, in particular sodium bicarbonate, is preferably used. Suitable amounts are 0.1-10 mol %, preferably 0.5-5 mol %, based on the diamine of the formula II.

Reaction stage (ii) is preferably carried out at reduced pressure, advantageously under azeotropic conditions at temperatures between 30° and 70° C., preferably 40° and 55° C. The pressure should be chosen so that epichlorohydrin and water can be distilled azeotropically. While the water is removed continuously from the system via a water separator, the epichlorohydrin is recycled to the reaction mixture (distillation with circulation).

Simultaneously with this distillation with circulation and the continuous removal of the water, the alkali metal or alkaline earth metal hydroxide solution is slowly added. The addition is advantageously effected uniformly in a period of $\geq 3$ hours with vigorous stirring.

Working up is carried out in principle in a known manner. Water extraction has proved particularly advantageous. This makes it possible to obtain particularly pure products in a virtually quantitative yield.

The epoxy resins containing N-glycidyl groups and obtained by the present process can be cured in a conventional manner. The present invention also relates to products, for example mouldings or fibre-reinforced composites, which contain a substance produced by curing the epoxy resin obtained in the process according to the invention. Suitable curing agents for epoxy resins containing N-glycidyl groups are well known: they include, for example, dicyanodiamide, aromatic amines, such as bis(3-aminophenyl) and bis(4-aminophenyl) sulfone and bis(4-aminophenyl)methane (generally together with a curing accelerator, for example a $BF_3$ amine complex), and anhydrides of polycarboxylic acids, such as cyclohexane-1,2-dicarboxylic anhydride, methylbicyclo[2.2.1]hept-5-ene-2,3-dicarboxylic anhydride and benzophenonetetracarboxylic dianhydride.

EXAMPLE 1

1300 g of epichlorohydrin are heated to 98°-100° C. with vigorous stirring in a 1500 ml reaction flask having a bottom outlet, and 85 g of 3,3'-diethyl-4,4'-diaminodiphenylmethane are metered in within 10 min. After a further 10 min, 169.3 g of 3,3'-diethyl-4,4'-diaminodiphenylmethane are added at the same temperature in the course of 60 min. The reaction solution is stirred for 6½ h at 98°-100° C. and then cooled to 50° C. 5 g of tetramethylammonium chloride, in the form of a 50% aqueous solution, and 15 g of sodium bicarbonate are then added. Epichlorohydrin is distilled at an internal temperature of about 44°-50° C. by means of a vacuum of about 85 mbar while being circulated via a water separator, and at the same time 328 g of a 50% aqueous solution of sodium hydroxide are uniformly metered in within 300 min. After the addition, distillation is continued for a further 30 min and the mixture is then cooled to 35° C. At 35° C., 700 g of water are added and the mixture is stirred for 5 min and then allowed to stand to achieve phase separation. The lower aqueous salt solution is separated off after 15 min. 200 g of water and a 50% aqueous solution of 5 g of sodium bisulfate are added to the organic phase in the reactor, and the mixture is stirred for 5 min and allowed to stand for 15 min to achieve phase separation. The lower organic phase is separated off and is extracted with 200 g of water in a separating vessel. After separation, the excess epichlorohydrin is distilled off at a temperature of up to 120° C. and in vacuo. Finally, the volatile constituents are stripped off with 30 g of water, and the product is dried for 60 min at 120° C., cooled to 80° C. and filtered with 5 g of the filtration aid Celatom 80 over a Suprafilter 200.

The yield is about 98% of theory, based on 3,3'-diethyl-4,4'-diaminodiphenylmethane. The epoxy content corresponds to 7.95 equivalents/kg, saponifiable chlorine corresponds to about 400 ppm and the Höppler viscosity at 25° C. corresponds to 9000 mPa.s.

EXAMPLE 2

The procedure is carried out as described in Example 1, except that the 3,3'-diethyl-4,4'-diaminodiphenylmethane is added in one portion. The results obtained are virtually identical to those obtained in Example 1.

EXAMPLE 3

Example 1 is repeated, except that the tetramethylammonium chloride used there is replaced with tetrabutylammonium chloride. The epoxy resin obtained has an epoxy content of 7.75 equivalents/kg, a saponifiable chlorine content of about 100 ppm and a Höppler viscosity at 25° C. of 9200 mPa.s.

EXAMPLE 4

Example 2 is repeated, except that the 3,3'-diethyl-4,4'-diaminodiphenylmethane used there is replaced with 282 g of 4,4'-methylenebis(2-methyl-6-ethylaniline). This gives an epoxy resin having an epoxy content of 7.3 equivalents/kg and a Höppler viscosity at 25° C. of 48,700 mPa.s.

EXAMPLE 5

Example 2 is repeated, except that the 3,3'-diethyl-4,4'-diaminodiphenylmethane used there is replaced with 310 g of 4,4'-methylenebis(2,6-diethylaniline). An epoxy resin having an epoxy content of 6.09 equivalents/kg and a Höppler viscosity at 25° C. of 40,500 mPa.s is obtained. The epoxy resin tends to crystallise.

What is claimed is:

1. A process for the preparation of a compound of the formula I

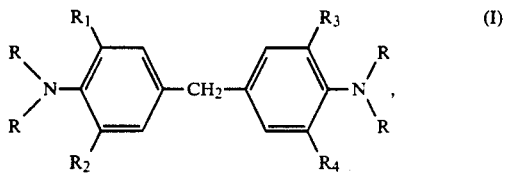

in which R is glycidyl, $R_1$ and $R_3$ independently of one another are $C_1$–$C_6$alkyl and $R_2$ and $R_4$ independently of one another are hydrogen or methyl, wherein (i) a diamine of the formula II

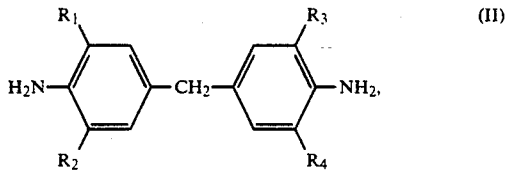

in which $R_1$, $R_2$, $R_3$ and $R_4$ are as defined above, is reacted with epichlorohydrin in the absence of catalyst in a molar ratio of 1:12 to 1:40 at a temperature of 80° to 115° C. and (ii) a phase transfer catalyst and a weak inorganic base are mixed with the reaction mixture at 30°–70° C., the epichlorohydrin is subjected to distillation while being circulated and at the same time the dehydrochlorination is carried out with the addition of a concentrated, aqueous alkali metal or alkaline earth metal hydroxide solution and simultaneous removal of the water distilled off azeotropically, and wherein said weak inorganic base is an alkali metal bicarbonate.

2. A process according to claim 1, wherein, in stage (i), the molar ratio of diamine of the formula II to epichlorohydrin is 1:12 to 1:20.

3. A process according to claim 1, wherein, in stage (i), the temperature is 90°–105° C.

4. A process according to claim 1, wherein 4–5 mol of alkali metal or alkaline earth metal hydroxide are used per mol of diamine of the formula II in stage (ii).

5. A process according to claim 1, wherein, in stage (ii), the phase transfer catalyst is a tertiary ammonium or phosphonium salt.

6. A process according to claim 1, wherein stage (ii) is carried out at reduced pressure.

7. A process according to claim 1, wherein, in stage (ii), the temperature is 40°–55° C.

8. A process according to claim 1, wherein, in formula (I), the substituents $R_1$ and $R_3$ or $R_2$ and $R_4$ have the same meaning.

9. A process according to claim 1, wherein, in formula (I), the substituents $R_2$ and $R_4$ are hydrogen.

10. A process according to claim 1, wherein, in formula (I), the substituents $R_1$ and $R_3$ are ethyl.

11. A process according to claim 1 wherein said weak inorganic base is sodium or potassium bicarbonate.

12. A process according to claim 1 wherein said weak inorganic base is sodium bicarbonate.

* * * * *